United States Patent [19]

Flesher et al.

[11] Patent Number: 4,889,610

[45] Date of Patent: Dec. 26, 1989

[54] POP UP ELECTROPHORESIS APPARATUS AND METHOD

[75] Inventors: Robert W. Flesher, Baltimore; Mark S. Berninger, Gaithersburg; Robert W. Blakesley, Frederick, all of Md.

[73] Assignee: Life Technologies, Inc., Gaithersburg, Md.

[21] Appl. No.: 219,930

[22] Filed: Jul. 15, 1988

[51] Int. Cl.[4] .................. G01N 27/28; G01N 27/26
[52] U.S. Cl. ...................... 204/299 R; 204/182.8
[58] Field of Search ............ 204/299 R, 182.8, 182.9, 204/180.1

[56] References Cited

U.S. PATENT DOCUMENTS

| | | | |
|---|---|---|---|
| 3,932,265 | 1/1976 | Hoefer | 204/299 R |
| 4,035,377 | 7/1977 | Detroy | 204/299 R |
| 4,049,534 | 9/1977 | Posner | 204/299 R |
| 4,151,065 | 4/1979 | Kaplan et al. | 204/299 R |
| 4,234,400 | 11/1980 | Kaplan et al. | 204/182.8 |
| 4,292,161 | 9/1981 | Hoefer et al. | 204/299 R |
| 4,473,452 | 9/1984 | Cantor et al. | 204/182.8 |
| 4,574,040 | 3/1986 | Delony et al. | 204/299 R |
| 4,588,491 | 5/1986 | Kreisher et al. | 204/182.8 X |
| 4,618,408 | 10/1986 | Malavarca et al. | 204/299 R |
| 4,624,768 | 11/1986 | Yoshida et al. | 204/299 R |
| 4,657,655 | 4/1987 | Smoot et al. | 204/299 R |
| 4,693,804 | 9/1987 | Serwer | 204/299 R X |

OTHER PUBLICATIONS

Advertisement entitled "Astec Band-It" (Mechanical Drawing Dated Mar., 1987, Citing U.S. Pat. No. 4,618,408 to Malavarca et al., issued 10/1986.
"Analysis of Restriction Fragments of T7 DNA and Determination of Molecular Weights by Electrophoresis in Neutral and Alkaline Gels," McDonell et al., J. Md. Biol. (1977), 119–146.
"Separation of Chromosome-Sized DNA Molecules by Pulsed Field Gel Electrophoresis," Lex H. T. Van Der Ploeg, (Jan./Feb. 1987).

Primary Examiner—John F. Niebling
Assistant Examiner—John S. Starsiak, Jr.
Attorney, Agent, or Firm—Saidman, Sterne, Kessler & Goldstein

[57] ABSTRACT

An apparatus provides for casting a gel and for presenting the gel for electrophoresis. The apparatus comprises a casting tray and the casting plate which combine to form a mold for the gelable liquid, and an electrophoresis tank in which the electrophoresis process occurs. The floor of the electrophoresis tank rises to form the plate pedestal upon which the casting plate rests during electrophoresis. The floor of the electrophoresis tank forms a cavity at the edges of the plate pedestal in which the casting tray rests during the electrophoresis process. The casting plate is first firmly seated in the bottom of the casting tray forming a mold for the gelable liquid. The gelable liquid is poured into the mold. The comb is placed in the comb slots so as to form wells in the gel. The gelable liquid is allowed to gel, and the comb is removed. The material to undergo electrophoresis is placed in the wells left by the comb. The entire assembly is then placed and aligned on the plate pedestal. The casting tray is then pushed down into the casting tray well. Electrophoresis buffer sufficient to fill the tank to approximately the top of the gel is then poured into the electrophoresis tank. An alternate embodiment is shown.

20 Claims, 7 Drawing Sheets

POP UP ELECTROPHORESIS APPARATUS AND METHOD

BACKGROUND OF THE INVENTION

1. Field of the Invention

This invention relates to devices and methods for forming gels for electrophoresis and for performing electrophoresis using those gels. More specifically, the invention relates to devices and methods for facilitating electrophoresis in horizontally oriented gels.

2. Related Art

Electrophoretic separation of nucleic acids in agarose gels is an important technique which is commonly used in molecular biology research and genetic diagnosis.

Many devices have been designed to facilitate gel electrophoresis of biologically significant macromolecules. Some of these devices are designed so as to orient the gel vertically. Other devices are designed to orient the gel horizontally.

A vertical orientation for the gel was generally preferred for the electrophoresis of nucleic acids in such applications as nucleic acid sequencing. The disadvantages of devices employing vertical orientation of the gel caused them to be replaced for many other applications by devices in which agarose gels were cast on a horizontal surface so that the electrophoretic separation occurred in a substantially horizontal direction To cast a horizontal gel, one must seal the ends of a gel casting deck onto which the heated molten gel material is poured. The end sealed casting deck thus provides a shallow cavity in which the molten agarose can cool and gel. Furthermore, to run an agarose gel, it is necessary to have effective and uniform electrical contact between the gel and the electrophoresis buffer at the ends of the gel. Several known devices have been used to cast horizontal agarose gels.

A first approach to casting horizontal gels makes use of "wicks" of agarose cast in chambers at each end of the platform upon which "separation" agarose gel is later cast. The wicks seal in the molten agarose during the casting procedure. The wicks provide an effective electrical connection between the separation gel and buffer reservoirs located on the outside of the respective wicks. An apparatus which typifies this design is disclosed in U.S. Pat. No. 4,234,400 to Kaplan et al.

Another approach adopted by designers of horizontal gel electrophoresis devices employs a removable tray (or deck) upon which the agarose gel could be cast. Certain of these devices cast a gel in an apparatus separate from that used to carry out the actual electrophoresis. Typically, the deck in which the agarose gel is cast consists of two opposing sides and two open ends which, when the gel is being used to electrophoretically separate macromolecules, will be directly exposed to the buffer. Commonly, this deck is situated between two reservoirs which contain a buffered salt solution. Electrodes are installed into the respective reservoirs to provide electrical current from a power supply. The two open ends of the deck allow effective and uniform electrical contact between the gel and the buffer. To cast the gel in the first place, however, it is necessary to seal these open ends of the deck to create a fluid-tight cavity for containing the molten agarose solution before it cools and gels.

To use this gel after hardening, the seals at the ends of the casting deck first have to be removed. A first method used to block the open ends of the gel casting deck during the gel cooling and hardening process consists of sealing the ends of the deck with an adhesive tape. The tape is peeled off before installing the gel in the electrophoresis apparatus. Unfortunately, the removal of the tape is time consuming and requires that the gel be manually picked up. Any such manipulation or other disturbance to the gel is undesirable, since agarose gels are fragile.

A second method of blocking the open ends of the casting deck during the gelation process consists of placing rectangular blocks into slots cut into the side walls of the electrophoresis apparatus. These blocks are thereby positioned against the open ends of the deck, providing a surface which seals the open ends of the deck during the casting. Unfortunately, to achieve a reliably tight seal against the ends of the deck is difficult, since the reliability of the seal in this technique is dependent on the exact positioning of the side wall slots and the exact size and shape of the rectangular blocks. This rectangular block design requires that the device be constructed with very tight manufacturing tolerances which have to be maintained throughout the life of the device. Such tight tolerance requirements cause increased manufacturing costs.

U.S. patent application Ser. No. 081,692 filed Aug. 4, 1987, now U.S. Pat. No. 4,830,725 assigned to a common assignee, discloses a method and apparatus which uses wedges instead of blocks to seal the ends of the deck. Using wedges solves many of the problems associated with blocks and tape.

U.S. Pat. No. 4,473,452 to Cantor et al. discloses an apparatus for and method of electrophoretically separating particles by electric fields which are transverse to each other, which alternate between respective high and low intensities out of phase with each other at a frequency related to the mass of the particles, and which move the particles in an overall direction transverse to the respective directions of the fields.

U.S. patent application Ser. No. 876,523 filed Aug. 13, 1986, now abandoned is directed toward a method and apparatus for manipulating the shape and orientation of electric fields for the purpose of controlling the migration particles in a gel. The invention described in the '523 Application is partly predicated on the discovery that the limitations inherent in the existing electrophoretic separation techniques can be overcome by applying contour-clamped homogeneous or inhomogeneous electric fields. The electric fields are generated by a method in which multiple electrodes are arranged on a closed-contour and clamped to predetermined electric potentials. The '523 Application has greatly enhanced the usefulness of electrophoresis as a research tool. DNA molecules up to or greater than 2 megabases in size can now be separated with high resolution. DNA molecules less than 50 kilobase in size can now be separated without distortion even at high voltage.

Previous electrophoresis techniques only use fields in one direction. Therefore only two opposite sides of the gel needs to be in electrical contact with the buffer. The recent advances in electrophoresis techniques as disclosed by the '523 Application utilize electric fields in more than one direction.

Therefore, when utilizing the electrophoresis techniques taught in the '523 Application, the agarose gel must have direct contact with the electrophoresis buffer on all of its horizontal edges. A simple, economic, repeatable, and convenient means for sealing and unsealing all the sides of gel casting decks and presenting that gel for electrophoresis is therefore desirable in order to practically implement those advances.

One method currently in use for casting gels with all their horizontal edges exposed is to apply adhesive tape to the edges of a rectangular sheet of glass or plexiglass so as to form a shallow pan. The molten gel is then poured into the "pan". After the gel has cooled and solidified, the tape is carefully removed The above described technique has many shortcomings. It is time consuming. It can easily lead to damaged and unusable gels if the tape is not removed with a large degree of care. Finally, it provides no practical means of transporting the gel about the laboratory after the electrophoresis has taken place without the fear that the slightest mishap will cause the gel to slide off the glass and onto the floor.

Other known techniques for casting gels with all their horizontal edges exposed use the electrophoresis tank itself as part of the casting apparatus. These techniques have the drawback of not allowing multiple gels to be cast in advance and thereby maximize the usage of the electrophoresis equipment. Furthermore, removing the gel from the electrophoresis tank and transporting the gel are often quite difficult. During removal and transport of the gels, they can easily be damaged if not handled with the utmost care. If a gel is damaged, the entire casting and electrophoresis processes may have to be repeated to ensure reliable test results Another problem present in known electrophoresis devices relates to the difficulty in referencing the "combs" which are used to create "wells" in the agarose gel into which samples are placed. Many known devices are designed so that, when the teeth of the combs are inserted into the molten agarose, the combs rest on surfaces which are physically remote from the casting deck. This remote referencing results in nonuniform and inaccurate separation of the ends of the teeth from the floor of the casting deck due to unreliable fitting of adjacent parts in the apparatus. This nonuniformity and inaccuracy in the placement of the combed teeth results in the creation of wells in the gel which are commensurately nonuniform and inaccurate. At times, the teeth of combs in known devices actually contact the floor of the casting deck, so that there is no agarose seal between the well and the casting deck after the agarose had gelled. The lack of an agarose gel seal sometimes precludes obtaining valuable experimental results.

It is therefore desirable to have a comb reference surface which substantially guarantees the uniformity and accuracy of the depth of wells in agarose gels, and thereby ensures the presence of agarose seals at the bottom of the wells Such a reference surface would reduce the manufacturing tolerances needed to manufacture the apparatus.

SUMMARY OF THE INVENTION

The present invention provides a method and apparatus for casting a gel, for presenting the gel for electrophoresis, and combines the advantage of ease of manufacture of the apparatus with the advantage of ease of use. The apparatus comprises a casting tray and a casting plate which combine to form a mold for a gelable liquid (also referred to as "molten gel") and an electrophoresis tank in which the electrophoresis process occurs. The floor of the electrophoresis tank rises to form a plate pedestal upon which the casting plate rests during electrophoresis. The floor of the electrophoresis tank forms a cavity at the edges of the plate pedestal, herein called a casting tray well, in which the casting tray rests during the electrophoresis process.

The casting plate is first firmly seated in the bottom of the casting tray forming a mold for the gelable liquid. The gel is then poured onto the casting plate. A comb is placed in comb slots so as to form wells in the gel. The gel is allowed to harden, and the comb is removed. The material to undergo electrophoresis, if contained within an agarose plug, is placed in the wells left by the comb. If the material to under go electrophoresis is in solution, it is placed in the wells after the buffer has been added. The entire assembly is then placed and aligned on the plate pedestal within the electrophoresis tank. The casting tray is then pushed down into the casting tray well so that no portion of it is within the plane of the gel. A quantity of electrophoresis buffer sufficient to fill the tank to approximately the top of the gel is then poured into the electrophoresis tank. Electrophoresis can then be carried out using any of the various methods known in the art.

Alternatively, the electrophoresis tank may utilize a releasable fastening means to hold the casting plate so the casting tray may be pulled up and away from the casting plate In this alternative embodiment, the electrophoresis tank's plate pedestal is replaced with a depression. The releasable fastening means is attached to the floor of the depression. In this alternative embodiment, the casting plate is releasably fastened to the floor of the depression instead of resting on the plate pedestal.

BRIEF DESCRIPTION OF THE DRAWINGS

The present invention is best understood by reading the following detailed description of the preferred embodiments in conjunction with the attached drawings, in which.

DETAILED DESCRIPTION OF THE PREFERRED EMBODIMENTS

I. Brief Overview

Figure 1:
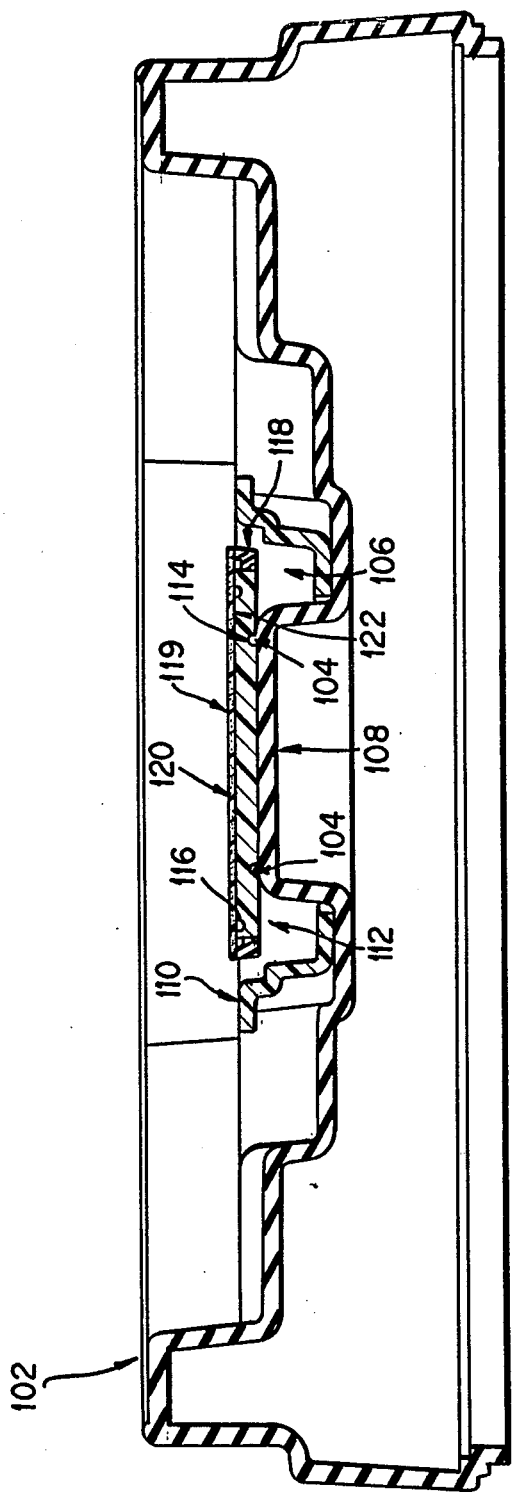
FIG. 1 is a cut-away side view of the electrophoresis tank showing the casting plate and the gel casting on the plate pedestal and the casting tray resting in the resting tray well according to the preferred embodiment of the present invention.

The present invention provides an apparatus and method for casting a gel, for presenting the gel for electrophoresis, and combines the advantage of ease of manufacture of the apparatus with the advantage of ease of use. It should be noted that in the preferred embodiment casting an agarose gel is the preferred use. The apparatus comprises a casting tray and the casting plate which combine to form a mold for a gelable liquid (also referred to as "molten gel"), and an electrophoresis tank in which the electrophoresis process occurs. The floor of the electrophoresis tank rises to form a plate pedestal upon which the casting plate rests during electrophoresis. The floor of the electrophoresis tank forms a cavity at the edges of the plate pedestal, herein called a casting tray well, in which the casting tray rests during the electrophoresis process.

The casting plate is first firmly seated in the bottom of the casting tray forming a mold for the gelable liquid. The gel is then poured into the casting plate. The comb is placed in the comb slots so as to form wells in the gel. The gelable liquid is allowed to gel, and the comb is removed. The material to undergo electrophoresis, if contained within an agarose plug, is placed in the wells left by the comb. If the material to undergo electrophoresis is in solution, it is placed in the wells after the buffer has been added. The entire assembly is then placed and aligned on the plate pedestal within the electrophoresis tank. The casting tray is then pushed down into the casting tray well so that no significant portion of it is substantially within the plane of the gel. A quantity of electrophoresis buffer sufficient to fill the tank to approximately the top of the gel is then poured into the electrophoresis tank. Electrophoresis can then be carried out using any of the various methods known in the art.

Alternatively, the electrophoresis tank may utilize a releasable fastening means to hold the casting plate so the casting tray may be pulled up and away from the casting plate. In this alternative embodiment, the electrophoresis tank's plate pedestal is replaced with a depression. The releasable fastening means is attached to the floor of the depression. In this alternative embodiment, the casting plate is fastened (secured) to the floor of the depression instead of resting on the plate pedestal.

II. PREFERRED EMBODIMENT

A. Operating Environment

In its preferred embodiment the present invention would be employed in an electrophoresis apparatus utilizing the techniques taught in U.S. Pat. No. 4,473,452 and U.S. patent application Ser. No. 896,523 filed Aug. 13, 1986, which are incorporated by reference herein. Specifically, the preferred operating environment for the present invention is an electrophoresis apparatus utilizing the embodiment disclosed in FIG. 2 of the '523 Application. It should be noted that the present invention is equally applicable in other known or future electrophoresis field arrangements and configurations.

Figure 2:
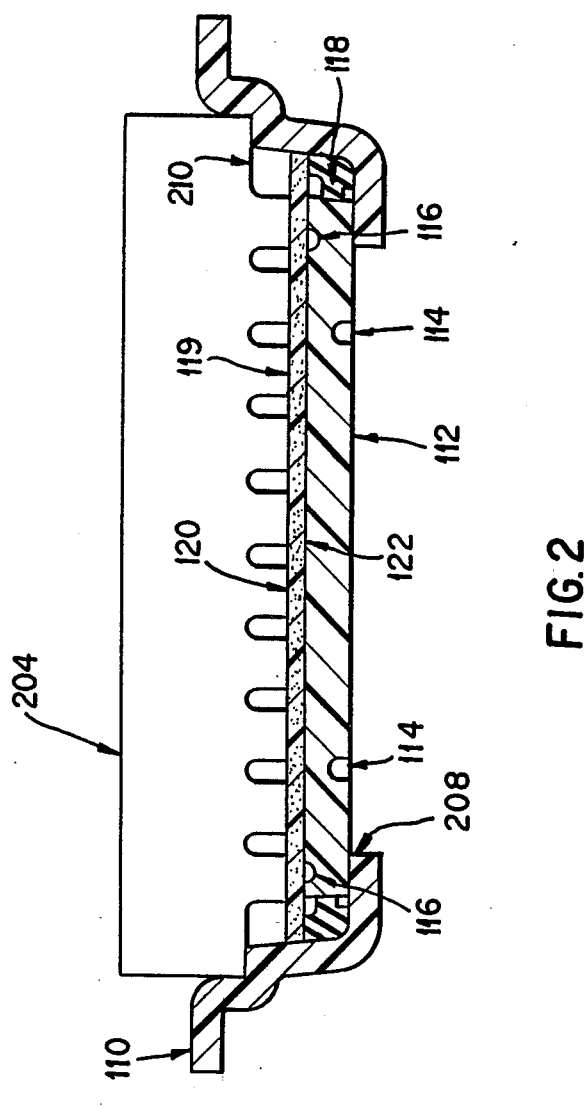
FIG. 2 is a cut-away side view of the casting deck assembly where the gel is cast according to the preferred embodiment of the present invention.

In the embodiment disclosed in FIG. 2 of the '523 Application, the field generating electrodes are arranged in a closed contour in the shape of a hexagon. Opposed sets of equally spaced electrodes are disposed on each side of the hexagon. All three of the opposed sets of electrodes are utilized to create the electric fields as described in the above named application.

Because the field is generated by electrodes on all four sides of the gel, the gel must maintain unimpeded electrical contact with the electrophoresis buffer on all four of its horizontal edges. The present invention simply and elegantly solves the problem of casting a gel with four exposed horizontal edges and presenting that gel for electrophoresis.

B. Structure

Turning now to a discussion of the preferred embodiment, reference will be made to FIG. 1. FIG. 1 is a cut-away side view of the electrophoresis tank, generally indicated as 102, according to the preferred embodiment of the present invention. The floor of electrophoresis tank 102 contains a depression, casting tray well 106, sufficient to hold the casting tray, to be described in more detail with reference to FIG. 2, in its submerged position. Located in approximately the middle of electrophoresis tank 102, is plate pedestal 108. Plate pedestal 108 contains alignment bumps 104 for aligning the casting plate, described in more detail with reference to FIG. 2. The electrophoresis tank can be advantageously formed of 0.22 Uniroyal series R59 (all measurements are in inches) made by Uniroyal of Akron, Ohio, but may be manufactured of any material which remains substantially inert and impervious to the chemical reactions which are to occur within it.

FIG. 2 is a cut-away side view of the casting deck assembly, which is used to cast the gel 119, according to the preferred embodiment of the present invention. Referring to FIG. 2, casting deck assembly comprises a casting tray 110, a casting plate 112, and an associated comb 204.

Comb 204 can be advantageously made from 0.18 or 0.25 white Delrin (made by DuPont of Washington, Del.), with the teeth machined to form wells of the desired size. The comb may alternatively be manufactured of any other material which is heat-resistant and smooth.

Casting tray 110 can be made of 0.187 clear acrylonitrile-butadiene-styrene (ABS), clear poly-vinyl-chloride (PVC), other thermoplastics (all of the preceding can be advantageously vacuum molded), or other suitable material which is substantially inert and impervious to the chemical reactions which occur within the electrophoresis tank.

Figure 3:
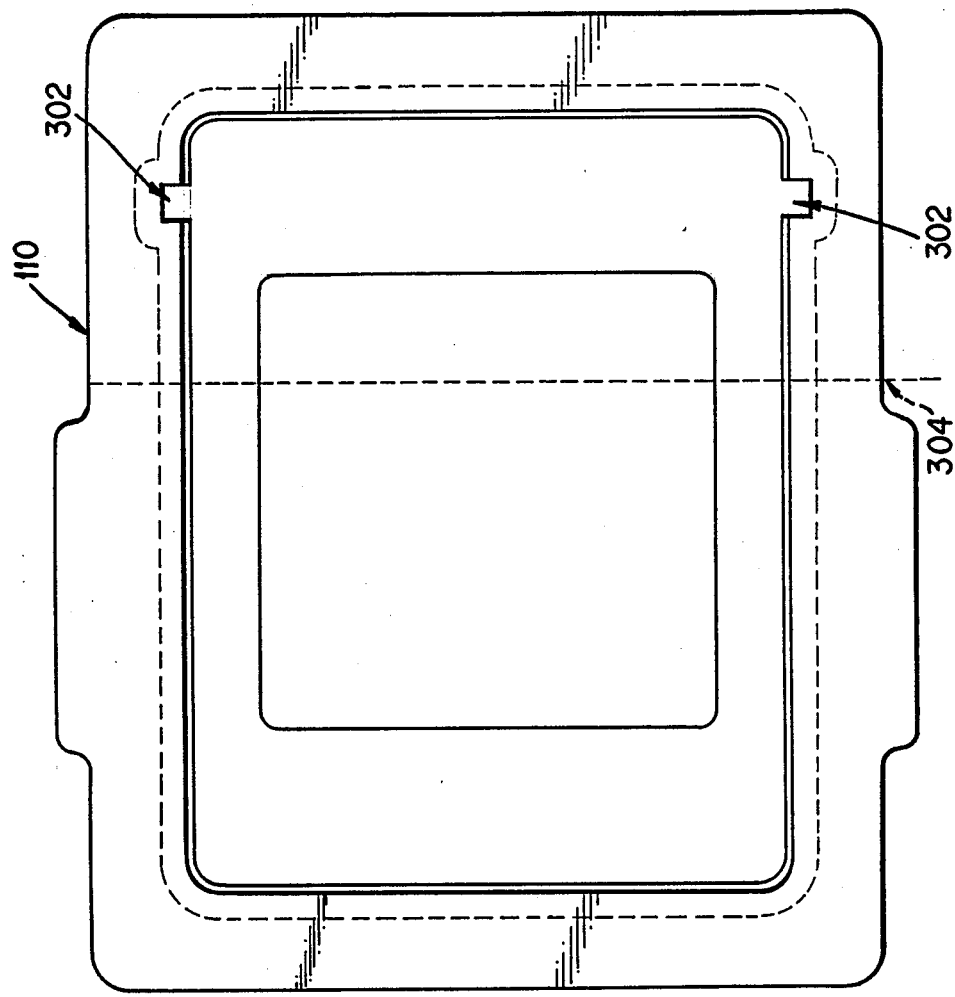
FIG. 3 is a top plan view of the casting tray, a subassembly of the casting deck assembly of FIG. 2 and shows a cut-away line 304 of the preferred embodiment of the present invention.
Figure 4:
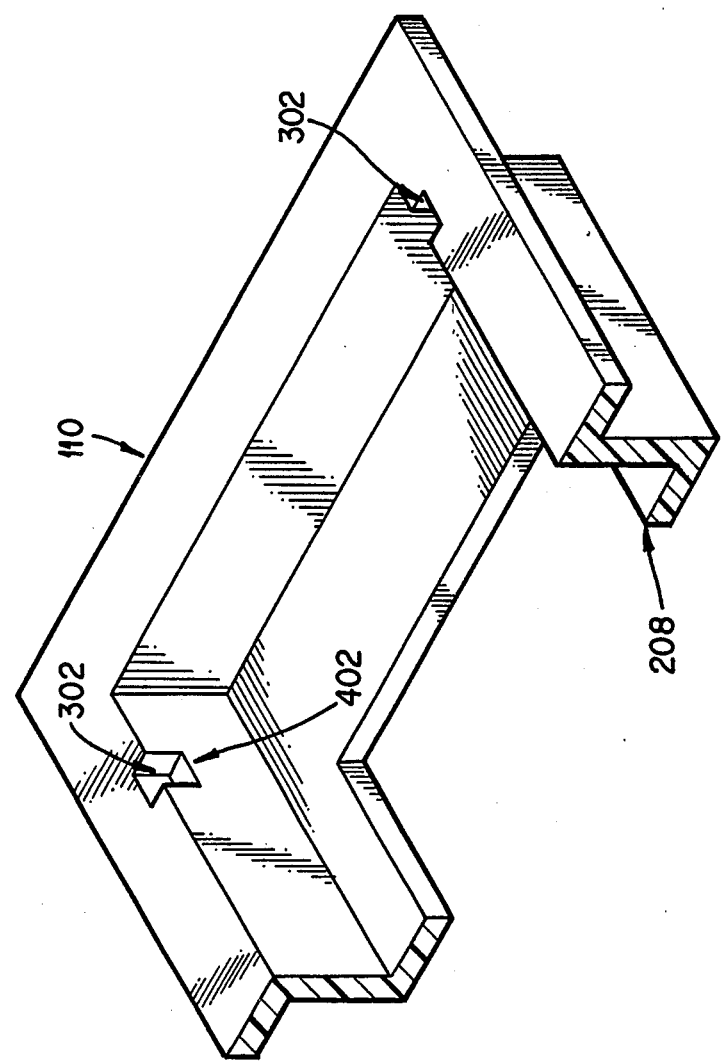
FIG. 4 is a partially cut-away perspective view of the casting tray of FIG. 3 taken along line 304 of FIG. 3.

FIG. 4 is a partially cut-away perspective view of casting tray 110 showing comb slots 302. FIG. 3, a top plan view of casting tray 110, shows cut-away line 304 which indicates the cut-away of FIG. 4. As shown in FIG. 4, comb 204 (see FIG. 2) can be firmly seated in comb slots 302 with the comb's teeth suspended above and not touching the bottom of the casting deck assembly. It is also contemplated that multiple comb slots may be employed (not shown) permitting a selection of well locations or multiple rows of wells if multiple combs are also employed.

It is important to the reliability of the experimental results that there be an agarose seal at the bottom of each well in the gel. This implies that the positioning of comb 204 must be reliably controlled so as to produce wells of uniform and proper depth. Wells of uniform and proper depths are consistently created when comb 202's comb seating surface 210 is in contact with comb reference surfaces 402.

Referring back to FIG. 2, casting plate 112 can be advantageously made of 0.25 clear UVT (ultraviolet transparent) acrylic, made by Rohm and Haas of Philadelphia, PA, but may be manufactured out of any material which is clear and which would not be significantly warped or deleteriously affected by repeated applications of molten agarose gel, e.g., glass.

Alignment holes 114, referring still to FIG. 2, are machined into casting plate 112 to facilitate alignment of casting plate 112 on the plate pedestal 108. Plate indentations 116 are machined into casting plate 112 so that the portion of the gel which flows into the plate indentations 116 will retard lateral movement of the gel during electrophoresis.

In the preferred embodiment as shown in FIG. 2, plate gasket 118, advantageously made of conventional urethane, is glued, using conventional glue for gluing urethane to clear UVT acrylic, to the edges of casting plate 112 (as shown in FIG. 1) to ensure a substantially fluid-tight seal between casting plate 112 and casting tray 110.

As an alternative (not shown) to employing plate gasket 118, a grooved channel or set of channels and matching projections may be employed to produce a substantially liquid-tight seal between the casting plate and the casting tray. Either the grooved channel or the projections may be located on the casting plate with the matching projections or grooved channel located on the casting tray. Other means for creating a substantially liquid-tight seal between the casting tray and the casting plate are also contemplated by the inventors.

Alternatively, plate gasket 118 could be made of any material which is highly resilient, is not substantially deleteriously effected by repeated applications of molten gel, and is substantially inert and impervious to the chemical reactions which occur within the electrophoresis tank. Other means could be used to effect a substantially fluid-tight seal between casting plate 112 and casting tray 110, e.g., machining casting plate 112 and casting tray 110 to a sufficiently high tolerance that they fit together, with no other material between them, perfectly enough to form a substantially fluid-tight seal.

C. Method of Use/Operation

The preferred method will now be discussed with reference primarily to FIG. 7, which shows the steps of the preferred method, with references made to the numbered elements of FIGS. 1-4. Casting plate 112 (with plate gasket 118 glued to its edges) is firmly seated in the bottom of casting tray 110 forming a substantially fluid-tight seal between casting plate 112 and casting tray 110, as noted in a step 702. When casting plate 112 is seated in casting tray 110, it rests on casting tray lip 208, shown in FIG. 2.

Casting tray 110 forms the walls for the mold into which the gelable liquid is to be poured and casting plate 112, along with plate gasket 118, form the floor of the mold. Step 702 also includes placing the assembly on a flat level surface to insure a gel of even depth.

In step 704 a sufficient quantity of gelable liquid to form a gel of the desired depth is poured into casting plate 112. The desired depth of the gel (generally indicated as 119 in FIG. 1) varies according to the requirements of the user. In step 706, comb 204 is then firmly seated in comb slots 302. (The normal depth of the gel is 0.25 inches, and the depth typically ranges from 0.125 inches to 0.50 inches.) Comb reference surfaces 402 located at the bottom of comb slots 302 (see FIG. 4) provide a constant alignment surface for comb seating surface 210 (see FIG. 2), located along the bottom edges near the end of comb 204, which results in wells that are of uniform shape and depth. (A typical well is dimensionally 0.250 inches by 0.100 inches by 0.100 inches in depth.) Wells larger or smaller than ones of the above dimensions may be preferred in particular applications, the preferred well size and configuration being largely related to the volume and character of the sample to be electrophoretically separated. The gelable liquid is allowed to gel in step 708. The arrangement of the apparatus after step 706 and during step 708 is pictured in FIG. 2.

Comb 204 is removed from comb slots 302 in step 710. This should be done by gently wiggling the comb to free the teeth from the gel and then slightly lifting up one side of the comb, then the other. If the sample to undergo electrophoresis is contained within an agarose plug, the plug should be carefully trimmed to the well dimensions and inserted into the well by forceps or spatula, as a part of step 712. If the plug is made from low melting point agarose, the plug should be placed in a microcentrifuge tube and melted at 65° C. The liquid should then be quickly pipetted directly into the well and allowed to solidify.

If the sample is in a solution, it is preferable to load it after step 718 has been performed. In other words, step 712 can be advantageously performed, in the case of liquid samples, after the electrophoresis buffer has been poured into electrophoresis tank 102.

In step 714 casting deck assembly 202 is placed in electrophoresis tank 102 on top of plate pedestal 108. The casting deck assembly is first grossly aligned on plate pedestal 108 by aligning the gross alignment space 206 under casting plate 112 and surrounded by casting tray 110 with the top of plate pedestal 108 and lowering the casting deck assembly onto plate pedestal 108. The gross alignment is performed in a manner similar to the manner in which the lid of a jar drops over the top of the jar with that casting deck assembly corresponding to the lid and plate pedestal 108 corresponding to the top. Casting deck assembly 202 is completely aligned on plate pedestal 108 when alignment bumps 104 are aligned with alignment holes 114, thus completing step 714. This is accomplished by gently sliding casting assembly 202 around as it rests on plate pedestal 108.

In step 716 casting tray 110 is gently pushed down into casting tray well 106 leaving casting plate 112 resting on plate pedestal 108. Gel 119 is now resting on top of casting plate 112 with all four of its horizontal edges exposed. The top plane of gel 119 is indicated as 120 and the bottom plane of the gel is indicated as 122 in FIG. 1.

Step 718 comprises pouring a quantity of electrophoresis buffer sufficient to fill electrophoresis tank 102 to a level which may barely submerge the gel. After steps 702 through 718 have been completed, the apparatus is now ready for the electrophoresis process to begin.

After the electrophoresis has been completed, casting tray 110 is lifted up, engaging casting plate 112, as noted in step 720. The gel may now be safely transported because it is safely contained within a walled container comprised of casting tray 110 and casting plate 112.

III. ALTERNATE EMBODIMENT

A. Structure

Figure 5:
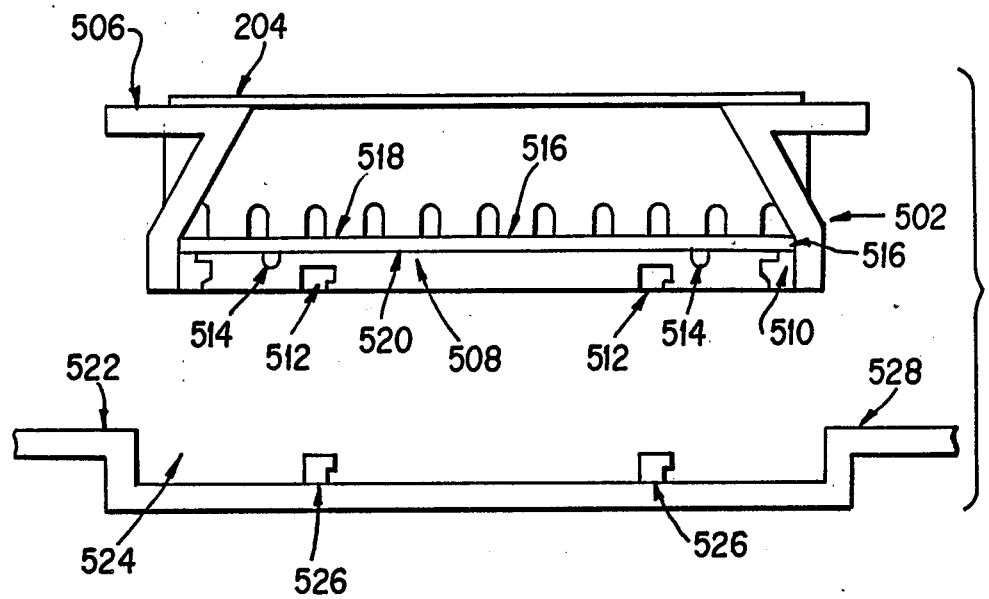
FIG. 5 is a cut-away side view of the casting deck assembly and a portion of the electrophoresis tank according to an alternate embodiment of the present invention.

Turning now to a discussion of an alternate embodiment, reference will be made to FIG. 5. FIG. 5 is a cut-away side view of a casting tray assembly and a portion of an electrophoresis tank according to an alternate embodiment of the present invention. Casting deck assembly 502 comprises casting tray 506, casting plate 508, and associated comb 204.

The alternate embodiment of FIG. 5 varies from the preferred embodiment in that casting tray 506 is intended to be pulled upward and free of casting plate 508 which would be releasably fastened to casting plate 508. Whereas, in the preferred embodiment shown in FIGS. 1-4, casting tray 110 is intended to be pushed down into casting tray well 106, free of casting plate 112 which would be resting on plate pedestal 108.

Still referring to FIG. 5, locking pins 526, located on the bottom of casting plate well 524, shown in FIG. 5, are L-shaped pins used to secure (fasten) casting plate 508 in casting plate well 524. Casting plate 508 has "L"-shaped locking holes 512 machined into it. Locking holes 512, together with locking pins 526, secure casting plate 508 to the floor of casting plate well 524. Alternatively, other means could be used to releasable secure casting plate 508 in casting plate well 524. Locking pins 526 and locking holes 512 are only meant to exemplify a releasable fastening means.

Casting plate 508, in the alternative embodiment under discussion, may be placed in casting plate well 524 so as to bring lower plane 520 of the gel 516 to the same level or higher than floor 528. Within casting plate well 524, locking pins 526 would be positioned so that after casting deck assembly 502 has been positioned to allow locking pins 526 to operatively engage locking holes 512 to secure the casting plate 508 to the electrophoresis tank, casting plate 508 and gel 516 are positioned substantially in the center of casting plate well 524. By so configuring locking pins 526, casting plate well 524, locking holes 512 and casting plate 508 in this manner, the symmetry of an electric field surrounding and penetrating gel 516 would be expected to be substantially maximized.

In the preferred embodiment of the alternative embodiment shown in FIG. 5, four locking pins 526 are utilized. The openings of locking holes 512 are large enough so that locking pins 526 may freely enter locking holes 512. Alternatively, more or fewer locking pins and corresponding locking holes may be employed.

Referring again to FIG. 5, electrophoresis tank 522 (only a portion of which is shown) has the same characteristics as electrophoresis tank 102 of FIG. 1, but lacks plate pedestal 108 and casting tray well 106.

Casting plate well 524 comprises an approximately rectangular depression in approximately the center of the floor of the electrophoresis tank. Casting tray 506 is large enough so that casting deck assembly 502 can rest in the depression and still have enough freedom to be shifted and thereby lock casting plate 508 with locking pins 526.

Casting plate well 524 is of a depth less than the height of casting plate 508. Therefore, when casting plate 508 is secured to the bottom of casting plate well 524 by locking pins 526, the bottom plane 520 of the gel 516 is substantially above the level of the floor of the electrophoresis tank.

Casting plate well 524, by allowing casting plate 508 to sit in a depression in the floor of electrophoresis tank 522 (only on portion of which is shown), requires the user to use less electrophoresis buffer. Alternatively, electrophoresis tank 522 could be made without casting plate well 524 and casting plate 508 could be releasably secured directly to the floor of electrophoresis tank. Of course, this would require the use of electrophoresis buffer sufficient to fill the electrophoresis tank up to the level equal to the height of casting tray 506 plus the height of the gel (to the level of the top plane of the gel, indicated as 518).

B. Method of Use/Operation

The method of operation of this alternate embodiment is quite similar to the method of operation of FIG. 7 of the preferred embodiment and will be described with reference to FIG. 8. Referring to FIG. 5, casting tray 506 is firmly mated to casting plate 508, creating a substantially liquid-tight seal in step 802. The seal is also of sufficient tightness to hold casting plate 508 snugly within casting tray 506. With casting plate 508 resting on a flat surface with plate indentations 514 facing upward, casting tray 506, with the larger opening facing downward, is firmly pressed downward and around the outside edges of casting plate 508. In step 804 gelable liquid is poured into the resulting mold and in step 806 the combs are inserted in a manner such as that described for the preferred embodiment.

After the gelable liquid has gelled in step 808, and the comb has been removed in a manner such as that described for the preferred embodiment, casting deck assembly 502 is lowered into casting plate well 524 (step 814). Locking holes 512 should be aligned with locking pins 526, allowing casting plate 508 to rest on the floor of casting plate well 524 (also step 814).

Figure 6:
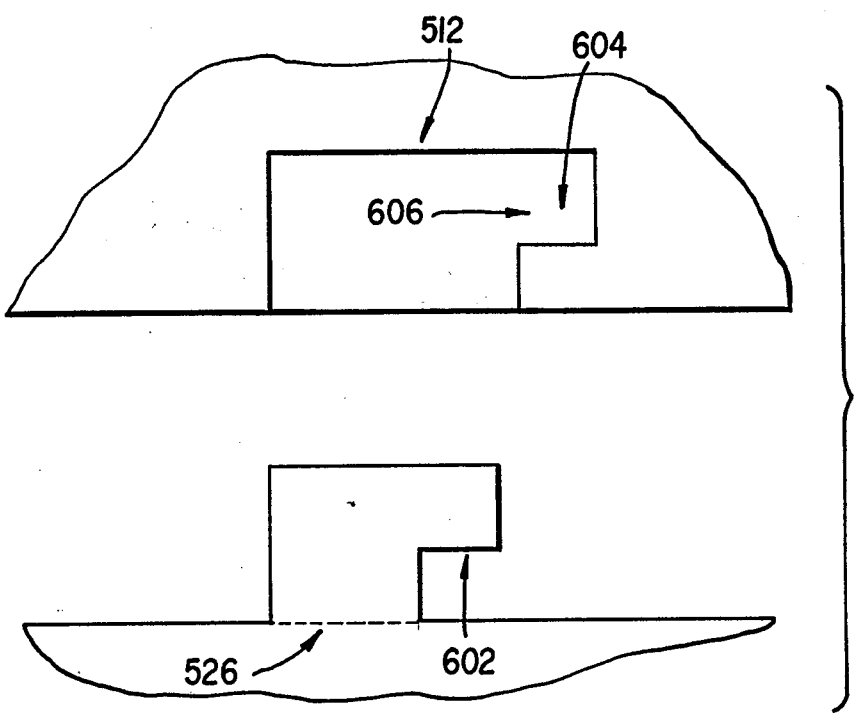
FIG. 6 is an expanded view of a locking pin and a locking hole from FIG. 5

In step 816, with locking pins 526 inside locking holes 512, casting deck assembly 502 should be shifted horizontally in a manner such that overhangs 602 (see FIG. 6) of locking pins 526 slide into the horizontal openings within locking holes 512. Therefore, when any upward pressure is exerted on casting tray 506, horizontal extensions 602 of locking pins 526 catch on lower surfaces 604 (see FIG. 6) of the horizontal holes 606 (see FIG. 6) of locking holes 512. Thus, casting plate 508 is secured to the bottom of casting plate well 524.

In step 818 casting tray 506 is gently pulled upward and free of casting plate 508. The portion of casting tray 506 which comes into contact with gel 516 may be angled inward (not shown) so that when casting tray 506 is pulled upward from casting plate 508, gel 516 is not substantially disturbed.

Electrophoresis buffer sufficient to nearly submerge gel 516, as described for the preferred embodiment, is then poured into the electrophoresis tank (step 820). The electrophoresis process can then occur (not shown as a step).

In step 822 after electrophoresis has occurred, casting tray 506 is re-mated to casting plate 508 by pressing casting tray 504 gently downward around casting plate 508. Also in step 822, casting deck assembly 502 is then shifted in such a manner that locking pins 526 disengage from horizontal holes 606 of locking holes 512, thus releasing casting plate 508. Casting deck assembly 502 can then be lifted out of casting plate well 524 (not shown as a step). Casting deck assembly 502 can then be used to safely transport gel 516.

IV. CONCLUSION

The present invention would also allow a laboratory which employed it to operate more efficiently. It is contemplated that one who uses this invention may purchase numerous casting deck assemblies. Possessing multiple casting deck assemblies would allow the user to cast multiple gels in advance of their use and to cast a gel in one casting deck assembly while electrophoresis is being performed on a gel in another casting deck assembly. This is possible because the gel is cast in an apparatus which is separate from the apparatus in which the electrophoresis is performed.

Figure 7:
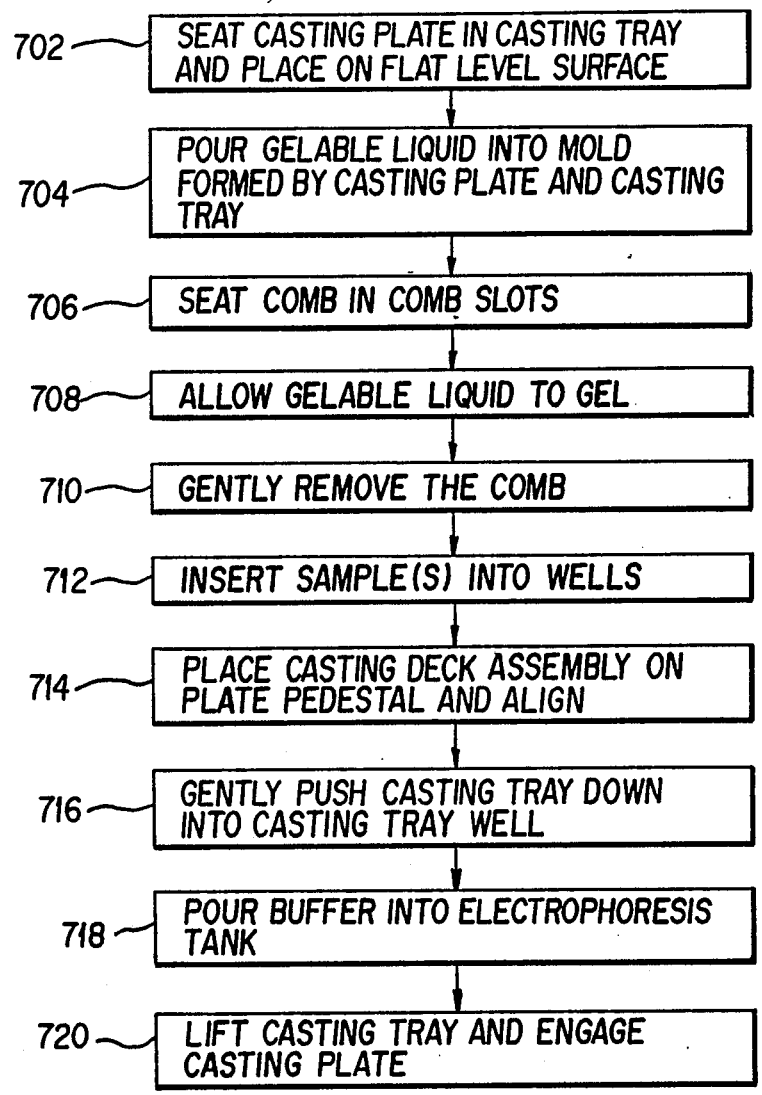
FIG. 7 is a flow chart of the preferred method of operation/use for the preferred embodiment of the present invention.
Figure 8:
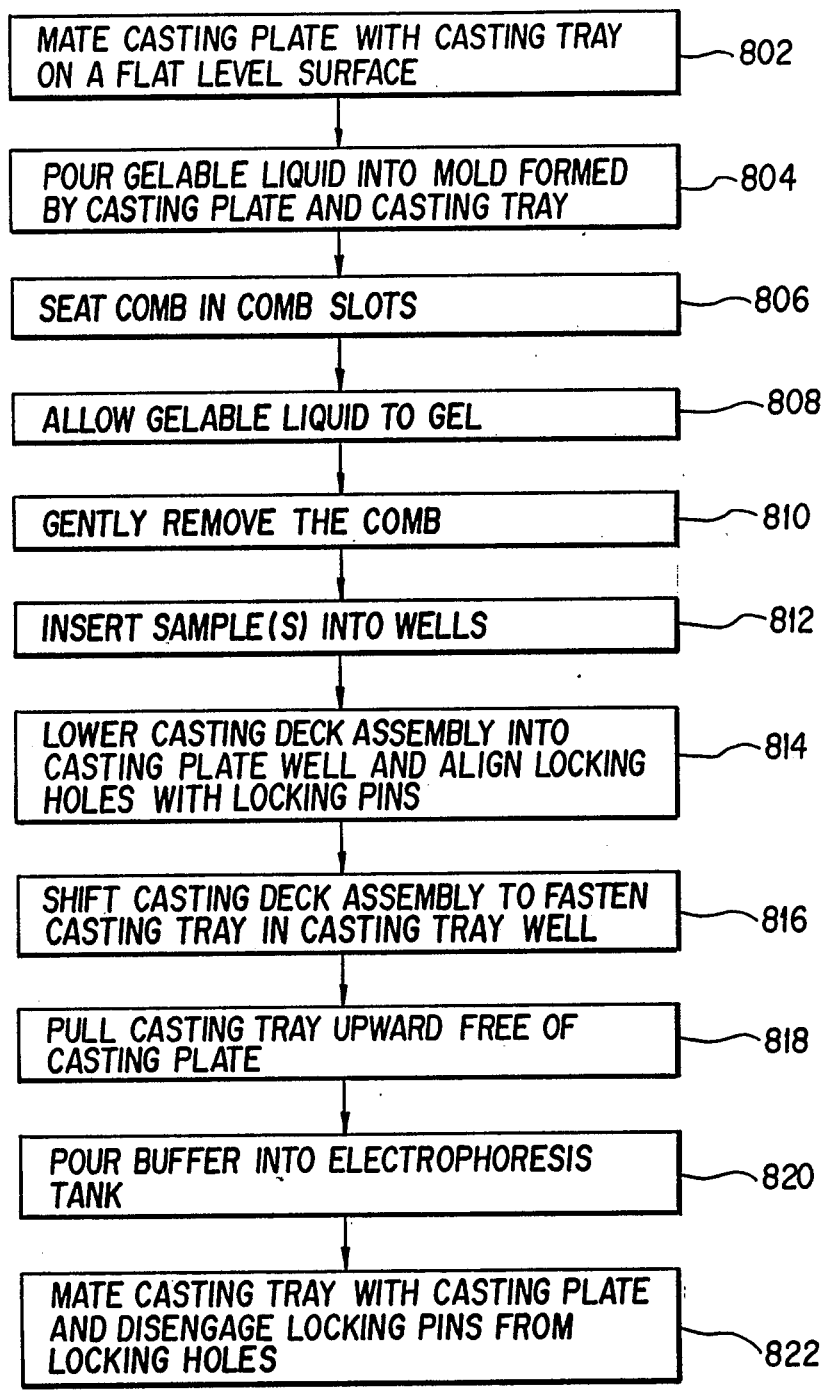
FIG. 8 is a flow chart of the preferred method of operation/use for the alternate embodiment of the present invention shown in FIG. 5.

Although the above description of FIG. 7 represents the preferred method and FIG. 8 represents the preferred method of an alternate embodiment, they are meant to be exemplary and not limiting. Most of the steps could be performed in a different order without affecting the ultimate result. For example, the comb could be seated in the comb slots (step 706 and step 806) prior to pouring the gel (step 704 and step 804) or even before the casting plate is seated in the casting tray (step 702 and step 802) without altering the end result.

It should be noted that the non-critical limitations of the above-described embodiments can be varied without having any substantial effect on the end result and the above described methods and embodiments are not intended to exclude those variations. For example, multiple combs and multiple comb slots could be employed to create multiple wells, or the shape of the casting plate could be altered to form different shaped gels. Various means could be employed to secure casting tray 506 to casting plate well 524 (both shown in FIG. 5) such as magnetic means or various types of mechanical fasteners other than those described above.

Although the present invention is especially suitable for the formation of agarose gels and subsequent electrophoresis processes which employ that gel, it can be used in any application where it is desirable to form a gel from a gelable liquid and secure that gel during the performance of a chemical experiment. It should be understood that the examples presented above are merely for purposes of illustration. Thus, the scope of the invention should not be limited by the exemplary embodiments described above, but should be defined only in accordance with the claims that follow.

What is claimed is:

1. An electrophoresis apparatus for forming a gel from a gelable liquid and for performing an electrophoresis process involving the gel, said electrophoresis apparatus comprising:
   a gel casting deck, said gel casting deck comprising a casting tray and a casting plate; and
   an electrophoresis tank;
   wherein said casting plate when mated with said casting tray forms a substantially liquid-tight mold for containing the gelable liquid during a gelation process;
   said plate being separable from said casting tray so that after the gelation process has occurred, the casting plate can be removed with the gel intact; and
   wherein said gel casting deck is placed within said electrophoresis tank, said gelation process occurs, and after said gelation process occurs, said casting plate is separated from said casting tray, leaving said casting plate and said gel within said electrophoresis tank.

2. An electrophoresis apparatus for forming a gel from a gelable liquid and for performing an electrophoresis process involving the gel, said electrophoresis apparatus comprising:
   a gel casting deck, said gel casting deck comprising a casting tray and a casting plate;
   an electrophoresis tank; and
   a plate pedestal and a casting tray well provided in said electrophoresis tank;
   wherein said casting plate when mated with said casting tray forms a substantially liquid-tight mold for containing the gelable liquid during a gelation process;
   said casting plate being separable from said casting tray so that after the gelation process has occurred, said casting plate can be removed with the gel substantially intact; and
   wherein said gel casting deck is placed on said plate pedestal within said electrophoresis tank, said gelation process occurs, and after said gelation process occurs, said casting plate is separated from said casting tray, leaving said plate and said gel on top of said pedestal and said casting tray substantially within said casting tray well within said electrophoresis tank.

3. An electrophoresis apparatus for forming a gel from a gelable liquid and for performing an electrophoresis process involving the gel, said apparatus comprising:
   a gel casting deck, said gel casting deck comprising a casting tray and a casting plate;
   an electrophoresis tank; and
   releasable fastening means for fastening said casting plate to said electrophoresis tank and for releasing said casting plate from said electrophoresis tank if said casting plate is fastened to said electrophoresis tank by said releasable fastening means;
   wherein said casting plate when mated with said casting tray forms a substantially liquid-tight mold for containing the gelable liquid during a gelation process;
   said plate being separable from said casting tray so that after the gelation process has occurred, the casting plate can be removed with the gel substantially intact;
   wherein said gel casting deck is placed within said electrophoresis tank; said casting plate is fastened to said electrophoresis tank by said releasable fastening means;
   said gelation process occurs, and after said gelation process occurs, said casting plate is separated from said casting tray, leaving said casting plate and said gel within said electrophoresis tank.

4. A method of forming a gel from a gelable liquid for placement in an electrophoresis tank, said method comprising the steps of:
   mating a casting plate with a casting tray so as to form a substantially fluid-tight seal therebetween and thereby defining a mold;
   pouring the gelable liquid into said mold, said mold's floor defined by said casting plate and said mold's walls defined by said casting tray;
   allowing the gelable liquid to gel, thereby forming a gel;
   placing said casting tray and said casting plate in the electrophoresis tank; and
   removing said casting tray from said casting plate so that the gel remains on said casting plate within said electrophoresis tank.

5. A method of forming a gel from a gelable liquid for placement in an electrophoresis tank having a plate pedestal and a casting tray well, said method comprising the steps of:

mating a casting plate with a casting tray so as to form a substantially fluid-tight seal therebetween and thereby defining a mold;

pouring the gelable liquid into said mold, said mold's floor defined by said casting plate and said mold's walls defined by said casting tray;

allowing the gelable liquid to gel, thereby forming a gel;

placing said casting tray and said casting plate in the electrophoresis tank upon said plate pedestal within said electrophoresis tank; and pushing down said casting tray into said casting tray well thereby separating said casting tray from said casting plate so that said gel remains on said casting plate within said electrophoresis tank and said casting tray remains substantially within said casting tray well.

6. A method of forming a gel on a casting plate from a gelable liquid for placement in an electrophoresis tank, wherein said casting plate and said electrophoresis tank are fastenable by releasably fastening means for releasable fastening, said method comprising the steps of:

mating a casting plate with a casting tray so as to form a substantially fluid-tight seal therebetween and thereby defining a mold;

pouring the gelable liquid into said mold, said mold's floor defined by said casting plate and said mold's walls defined by said casting tray;

allowing the gelable liquid to gel, thereby forming a gel; placing said casting tray and said casting plate in the electrophoresis tank;

fastening said casting plate to said electrophoresis tank by said releasable fastening means; and removing said casting tray from said casting plate so that the gel remains on said casting plate within said electrophoresis tank.

7. The apparatus according to claim 1, wherein said casting plate has at least one indentation for accepting the gelable liquid prior to gelation to substantially impede movement of the gel.

8. The apparatus according to claim 2, wherein said casting plate has at least one indentation for accepting the gelable liquid prior to gelation to substantially impede movement of the gel.

9. The apparatus according to claim 3, wherein said casting plate has at least one indentation for accepting the gelable liquid prior to gelation to substantially impede movement of the gel.

10. The apparatus according to claim 1, wherein said apparatus further comprises a comb; and said casting tray has comb reference surfaces for providing a constant alignment surface for said comb.

11. The apparatus according to claim 2, wherein said apparatus further comprises a comb; and said casting tray has comb reference surfaces for providing a constant alignment surface for said comb.

12. The apparatus according to claim 3, wherein said apparatus further comprises a comb; and said casting tray has comb reference surfaces for providing a constant alignment surface for said comb.

13. The apparatus according to claim 2, wherein said casting tray is substantially beneath the gel's lower plane when said casting tray is resting in said casting tray well and said casting plate, with the gel on top of it, is resting on said plate pedestal.

14. The apparatus according to claim 2, wherein a gross alignment space is defined by the underside of said casting plate surrounded by said casting tray, and said gross alignment space is used to grossly align said casting deck with said plate pedestal; and said plate pedestal further comprises alignment bumps on its top surface that fit into alignment holes located on the underside of said casting plate when final alignment has been obtained.

15. The apparatus according to claim 3, wherein said electrophoresis tank has a depression in approximately its center wherein said casting plate can be releasably fastened; and said releasable fastening means comprising at least one locking pin located on the floor of said depression and at least one locking hole located on the underside of said casting plate.

16. The method of claim 4, further comprising the steps of seating a comb in said mold prior to the gelable liquid becoming a gel; and removing said comb from said gel, after the gelable liquid has gelled, whereby wells of a substantially uniform shape and depth are formed in the gel.

17. The method of claim 5, further comprising the steps of seating a comb in said mold prior to the gelable liquid becoming a gel; and removing said comb from said gel, after the gelable liquid has gelled, whereby wells of a substantially uniform shape and depth are formed in the gel.

18. The method of claim 6, further comprising the steps of seating a comb in said mold prior to the gelable liquid becoming a gel; and removing said comb from said gel, after the gelable liquid has gelled, whereby wells of a substantially uniform shape and depth are formed in the gel.

19. The apparatus according to claim 1, wherein said casting tray further comprises comb slots for guiding a comb's seating surfaces to contact comb reference surfaces, located at the bottom of said comb slots, which provide substantially reliable control of the comb's positioning.

20. The apparatus according to claim 2, wherein said casting tray further comprises comb slots for guiding a comb's seating surfaces to contact comb reference surfaces, located at the bottom of said comb slots, which provide substantially reliable control of the comb's positioning.

* * * * *